United States Patent [19]

Schaeffer et al.

[11] Patent Number: 4,784,912
[45] Date of Patent: Nov. 15, 1988

[54] LATEX PARTICLES INCORPORATING STABILIZED FLUORESCENT RARE EARTH LABELS

[75] Inventors: James R. Schaeffer, Penfield; Tsang J. Chen, Rochester; Michael A. Schen, Wellsville, all of N.Y.

[73] Assignee: Eastman Kodak Company, Rochester, N.Y.

[21] Appl. No.: 112,302

[22] Filed: Oct. 26, 1987

Related U.S. Application Data

[62] Division of Ser. No. 713,202, Mar. 18, 1985, Pat. No. 4,735,907.

[51] Int. Cl.$^4$ ..................... B32B 27/32; G01N 33/546
[52] U.S. Cl. .................................. 428/402; 436/533; 436/534; 436/546; 436/805; 534/15
[58] Field of Search ................ 428/402; 436/533, 534, 436/546, 805; 534/15

[56] References Cited

U.S. PATENT DOCUMENTS 4,259,313  3/1981  Frank et al. ..................... 436/531
4,374,120  2/1983  Soini et al. ..................... 436/546

Primary Examiner—Robert J. Warden
Assistant Examiner—Robert Benson
Attorney, Agent, or Firm—J. Lanny Tucker

[57] ABSTRACT

Improved fluorescent labels comprise a fluorescent rare earth chelate incorporated into a polymeric particle derived from a loadable latex. The polymer comprises: (a) from about 50 to about 96 weight percent of recurring units derived from a hydrophobic ethylenically unsaturated polymerizable monomer, (b) from about 2 to about 30 weight percent of recurring units derived from a nonionic hydrophilic ethylenically unsaturated polymerizable monomer, and (c) from about 2 to about 20 weight percent of recurring units derived from an anionic ethylenically unsaturated polymerizable monomer containing at least one solubilizing group. The labels of this invention have greatly improved stability in aqueous solutions and do not prematurely agglomerate during storage. They can be attached to any of a variety of physiologically reactive species to provide labeled species, and are particularly useful in specific binding assays.

4 Claims, No Drawings

LATEX PARTICLES INCORPORATING STABILIZED FLUORESCENT RARE EARTH LABELS

This is a division of application Ser. No. 713,202, filed Mar. 18, 1985, now U.S. Pat. No. 4,735,907.

FIELD OF THE INVENTION

This invention relates to fluorescent labels and to fluorescent labeled physiologically reactive species useful in biomedical studies and clinical chemistry determinations. These labels and labeled species are particularly useful in specific binding assays, e.g. immunoassays, to determine a specific binding ligand, such as a hapten, in human biological fluids.

BACKGROUND OF THE INVENTION

In the fields of medicine and clinical chemistry, many studies and determinations of physiologically reactive species, e.g. cells, proteins, enzymes, cofactors, nucleic acids, substrates, antigens, antibodies, etc. are carried out using "labels" which facilitate the detection or separation of the materials under observation at low concentrations. In one such application, the diagnosis of pathological conditions and the detection of drugs or narcotics in humans and animals is often carried out using labeled materials in specific binding assays using competitive binding principles.

Whenever labels are used, sensitivity is of prime importance due to the generally low levels of biological species that are measured. Procedures carried out using radiometric labels generally do not have sufficient sensitivity for many low level analytes. In addition, radiometric labels suffer from the drawbacks of short useful life and handling hazards.

Labeling with magnetic iron oxide has also been proposed, as described in U.S. Pat. No. 4,452,773 (issued June 5, 1984 to Molday). The sensitivity of such labels is also limited, and their use in labeling biological species requires expensive equipment and tedious procedures.

Fluorescent spectroscopy, one of the most sensitive and versatile of the optical analytical techniques, has become increasingly popular in recent years to overcome the drawbacks of other labeling techniques. In fluorescence spectroscopy, a sample containing a fluorescent species is irradiated with light of known spectral distribution within the excitation spectrum of the target fluorescent species. The intensity of the resulting characteristic emission spectrum of the fluorescent target molecules is determined and is related to the number of target molecules present in the sample. Fluorescent spectroscopy is used extensively for studies of protein structure, bacterial cell wall reactions and conformational changes in enzymes, as well as for determinations of an immunologically reactive ligand in a specific binding assay.

Fluorescent labels comprising chelates of a rare earth element incorporated into polymeric particles of a latex are described in U.S. Pat. Nos. 4,259,313 (issued Mar. 31, 1981 to Frank et al) and related 4,283,382 (issued Aug. 11, 1981 to Frank et al). These labels exhibit improved efficiency in fluorescence and are particularly useful for immunoassays. The polymeric particles serve as carriers for immunologically reactive species directly attached thereto.

Although these labels represent a breakthrough in clinical chemistry because they have improved fluorescence efficiency, there is a need to render them more stable in aqueous solutions. The labels of Frank et al tend to agglutinate spontaneously and to settle out of solution. They therefore have a shortened storage life. They also demonstrate a tendency to agglutinate prematurely during an assay.

Attempts to improve the stability of fluorescent labels led our colleagues, B. A. Burdick and S. J. Danielson to discover improved fluorescent labels and labeled species which are the subject of copending and commonly assigned U.S. patent application Ser. No. 713,206, filed on Mar. 18, 1985 now U.S. Pat. 4,719,182 and entitled FLUORESCENT LABELS AND LABELED SPECIES AND THEIR USE IN ANALYTICAL ELEMENTS AND DETERMINATIONS. The novel materials of that application comprise a rare earth chelate incorporated into a polymeric particle like those of the Frank et al references noted above, but with the critical difference that a polysaccharide arm serves as a linkage between the polymeric particle and the physiologically reactive species. The polysaccharide arm provides improved stability in aqueous solutions which the Frank et al labels generally lack.

Despite the advantages of the materials containing the polysaccharide arm, it is substantially tedious and expensive to make them. Manufacture requires additional starting materials and additional steps of attaching the polysaccharide arm to both the polymeric particle and to the physiologically reactive species. It would be extremely desirable to achieve increased stability of fluorescent labels without the use of the polysaccharide linking arm and the problems associated with it.

SUMMARY OF THE INVENTION

We have discovered that certain fluorescent labels and labeled species having rare earth chelates incorporated therein are extremely stable in aqueous solutions. The materials of this invention do not prematurely agglomerate during either storage or use. These materials are particularly useful in specific binding assays, but they can also be used in a variety of biomedical studies where labeling of any physiologically reactive species is desired. These labels exhibit the desirably high sensitivity which accompanies the use of fluorescence spectroscopy. The unexpected and significantly improved properties of the materials of this invention are achieved because they are composed of polymers prepared from a specific combination of ethylenically unsaturated polymerizable monomers.

Therefore, in accordance with this invention, a fluorescent label comprises a fluorescent rare earth chelate incorporated into a polymeric particle which is derived from a loadable latex having a discontinuous phase and an aqueous phase. The discontinuous phase consists essentially of a polymer comprising:

(a) from about 50 to about 96 weight percent of recurring units derived from a hydrophobic ethylenically unsaturated polymerizable monomer, (b) from about 2 to about 30 weight percent of recurring units derived from a nonionic hydrophilic ethylenically unsaturated polymerizable monomer, and (c) from about 2 to about 20 weight percent of recurring units derived from an anionic ethylenically unsaturated polymerizable monomer containing at least one solubilizing group.

This invention also provides a fluorescent labeled physiologically reactive species. Such labeled species comprises a physiologically reactive species bound to the fluorescent label described above. In preferred embodiments, this labeled species is a labeled immunologically reactive ligand analog.

Further, this invention provides a dry analytical element which comprises an absorbent carrier material and the fluorescent labeled physiologically reactive species described above. In preferred embodiments, the absorbent carrier material is a porous spreading zone carried on a support.

Still further, this invention comprises a method for the determination of an immunologically reactive ligand in an aqueous liquid. The method comprises the steps of:

A. in the presence of a receptor for the ligand, contacting a sample of the liquid with a fluorescent labeled immunologically reactive ligand analog as described above, to form a complex between the receptor and the ligand analog, and B. fluorometrically detecting the ligand analog.

DETAILED DESCRIPTION OF THE INVENTION

The fluorescent labels of this invention can be used as probes, or labeling materials, for a variety of biomedical studies and clinical chemistry determinations. They can be used to label cells or other physiologically reactive species including proteins, nucleic acids (e.g. DNA), enzymes, enzyme substrates, cofactors, viruses, leukocytes, growth factors, lectins, antigens, antibodies, haptens, metabolites, hormones, toxins, radioisotopes, and others known to one skilled in the art. The labels are attached to such biological materials in a suitable manner, e.g. covalently or by absorption.

The labels are particularly useful in specific binding assays to determine an analyte (i.e. immunologically reactive species). In these assays, the species to be determined is attached to the label and the labeled species is placed in competition with unlabeled species from a test sample for reaction with a common reactant. The analyte to be determined is referred to herein as the ligand, the labeled analyte as the ligand analog. Compounds which specifically recognize the ligand and ligand analog and react to form complexes with them are referred to herein as receptors.

In performing one such type of assay, the ligand is placed in competition with the ligand analog for binding to the receptor. Unknown concentrations of the ligand are inferred from the measured signal of the labeled ligand analog. The complexation reaction proceeds as follows:

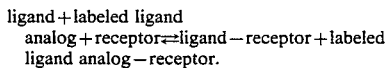

In preferred embodiments of this invention, the ligand is an antigen or antibody, the labeled ligand analog is a labeled antigen or antibody and the specific binding assay is an immunoassay. In the following discussion and presentation of examples, reference will be made primarily to these preferred embodiments, but it is to be understood that the scope of the invention is inclusive of any other specific binding assays.

The labels of this invention comprise latex polymer particles which contain a rare earth chelate. These labels are "aqueous-stabilized," which, in the context of this application means that the fluorescence of the chelate is not quenched in an aqueous environment.

In general, any fluorescent rare earth chelate which demonstrates fluorescent behavior is useful in the practice of this invention. In particular, the chelate comprises a rare earth metal (i.e. a lanthanide metal) such as europium or terbium. Europium is most preferred.

The chelate also includes a suitable chelating agent. Particularly useful chelating agents include 1,3-diketones (e.g. acetylacetonate, p-benzoylacetonate, p-benzoylbenzoate, trifluoro-2-furylacetylacetone, etc.), phthalates, naphthoates (e.g. dinaphthoylmethide, etc.), dipyridines (e.g. 2,2'-dipyridine-1,1'-dioxide, 4,4'-dimethyl-2,2'-dipyridine, etc.), terpyridines (e.g. 2,2',6',2''-terpyridine, etc.) and phenanthrolines (e.g. o-phenanthroline isothiocyanate, etc.). Other chelating agents are known to those skilled in the art. The 1,3-diketones are preferred.

The labels of this invention are prepared with loadable latices. The details of "loading" the latices useful in this invention are given in the Frank et al patents noted above. Generally, the chelates are incorporated in the polymer particles by gradually increasing the hydrophilicity of a solution of a chelate in a water-miscible solvent in the presence of uncoagulated, undissolved loadable polymeric latex particles to a point at which substantially no chelate remains dissolved in the water-miscible solvent. Up to about 7.5% (based on polymer weight) of chelate can be "loaded" or imbibed into the polymer particles in this manner. The concentration of chelate in the polymer particles will be varied to some extent depending upon the particular use of the label intended. The preparation of a fluorescent label of this invention is described in Example 1 below.

Loadable polymer latices useful herein are those which include a polymeric discontinuous phase (particles) which consists essentially of one or more polymers prepared from the ethylenically unsaturated polymerizable monomers described below, and an aqueous phase. The polymer particles of these latices generally have an average diameter of from about 0.01 to about 2 $\mu$m, and preferably from about 0.1 to about 0.5 $\mu$m. As used in this application, the term "loadable" has the meaning defined in the Frank et al patents.

The polymeric particles are copolymers comprising:

(a) from about 50 to about 96, and preferably from about 75 to about 92, weight percent of recurring units derived from one or more hydrophobic ethylenically unsaturated polymerizable monomers, (b) from about 2 to about 30, and preferably from about 5 to about 15, weight percent of recurring units derived from one or more nonionic hydrophilic ethylenically unsaturated polymerizable monomers, and (c) from about 2 to about 20, and preferably from about 3 to about 10, weight percent of recurring units derived from one or more anionic ethylenically unsaturated polymerizable monomers containing at least one solubilizing group.

Useful hydrophobic monomers of group (a) include vinyl aromatics, such as substituted or unsubstituted styrenes and vinyl naphthalenes, and acrylic and methacrylic acid alkyl esters. The substituted or unsubstituted styrenes are preferred. Representative monomers include styrene, α-methylstyrene, p-bromostyrene, vinyltoluene, 1-vinylnaphthalene, methyl acrylate, methyl methacrylate, ethyl methacrylate, n-butyl acrylate, propyl acrylate, and others known to one skilled in the art. These monomers are hydrophobic, meaning that they are generally insoluble in water (i.e. less than about 30 mg/ml of water). Styrene and vinyltoluene are particularly useful monomers.

The monomers of group (b) are nonionic but hydrophilic, i.e. they are water soluble or water dispersible (e.g. greater than about 100 mg/ml of water). They generally have one or more uncharged groups which are solubilizing, such as hydroxy, amide (substituted or unsubstituted), cyclic amide, sulfonamide and the like. Representative monomers include acrylamide, methacrylamide, N-isopropylacrylamide, 2-hydroxyethyl acrylate, 2-hydroxypropyl methacrylate, 2-acrylamido-2-hydroxymethyl-1,3-propanediol, N-methylmethacrylamide, N-vinylpyrrolidone and others known to one skilled in the art. Acrylamide, methacrylamide, N-isopropylacrylamide, 2-hydroxyethyl acrylate and 2-hydroxyethyl methacrylate are particularly useful, with the monomers containing amide groups most preferred.

Useful anionic monomers of group (c) include monomers having one or more negatively charged groups, e.g. carboxy, sulfo, phosphono, sulfino, and the like groups and corresponding salts. Preferably, the monomers contain one or more carboxy groups. Representative monomers include acrylic acid, methacrylic acid, itaconic acid, 2-acrylamido-2-methylpropane sulfonic acid, 3-methacryloyloxypropane-1-sulfonic acid, vinyl sulfonic acid, and alkali metal and ammonium salts of these acids, and others known to one skilled in the art. Acrylic acid, methacrylic acid and itaconic acid are particularly useful.

Representative polymers useful in the practice of this invention include poly(styrene-co-acrylamide-co-methacrylic acid) (85:10:5 weight ratio), poly(styrene-co-methacrylamide-co-methacrylic acid) (85:10:5 weight ratio), poly(vinyltoluene-co-N-isopropylacrylamide-co-itaconic acid) (65:20:15 weight ratio), poly(n-butyl acrylate-co-styrene-co-methacrylamide-co-methacrylic acid) (45:45:2:8 weight ratio), poly(methyl methacrylate-co-2-hydroxyethyl acrylate-co-acrylic acid) (90:5:5 weight ratio), poly(n-butyl acrylate-co-styrene-co-acrylamide-co-methacrylic acid) (54:38:5:3 weight ratio), poly(n-butyl acrylate-co-styrene-co-acrylamide-co-sodium 2-acrylamido-2-methylpropane-1-sulfonate) (15:50:30:5 weight ratio), and poly(n-butyl acrylate-co-styrene-co-methacrylamide-co-sodium 2-acrylamido-2-methylpropane-1-sulfonate) (20:45:30:5 weight ratio). The first polymer listed is a preferred polymer for use in this invention.

The loadable polymer latices used in preparing the fluorescent labels can be prepared using well known emulsion polymerization techniques. Generally, they are prepared using free radical initiated reactions of the monomers dispersed in an aqueous medium with one or more appropriate surfactants.

The labeled physiologically reactive species of this invention can be prepared by mixing the fluorescent label with the physiologically reactive species for a suitable time (e.g. up to 72 hours) to facilitate absorption of the species on the surface of the polymeric particles. Alternatively, the species can be covalently bonded to the surface of the polymeric particles by chemically modifying either or both the species and particles to provide suitable reaction sites. Details of the preparation of a representative labeled species are provided in Example 1 below.

The fluorescent labeled specific binding ligand analog of this invention can be used in specific binding immunoassays, particularly those which utilize temporal resolution of the specific detecting signal to distinguish it from background. In this immunoassay, a sample of test aqueous liquid is excited in an intermittent fashion and information is accepted only during the dark cycle when the long-lived fluorescent label is still emitting strongly but when other sources of fluorescence have decayed. Discontinuous excitation can be achieved in a variety of ways, including pulsed laser, mechanical chopping or a continuous excitation beam, moving the sample in and out of the excitation beam, etc. In general, fluorescent immunoassay techniques are known in the art.

In the practice of this invention, the labeled ligand analog indicates the amount of unknown ligand in the test sample. Either the bound or unbound fraction of labeled ligand analog can be measured.

To accomplish a specific binding assay, physical separation of bound and unbound ligand can be carried out using conventional techniques, if necessary.

In a solution assay, the fluorescent labeled specific binding ligand analog is generally present in a concentration of up to about 1, and preferably from about 0.01 to about 1, mg/dl of solution. The receptor corresponding to the ligand (or analyte) to be determined is generally present in an amount of up to about 1, and preferably from about $10^{-6}$ to about 1 g/dl of solution. Other materials, e.g. buffers, surfactants, etc. can be included in conventional amounts if desired.

The ligand analog and method of this invention are adaptable to both solution and dry element assays. The ligand analog, along with its receptor, can be provided as part of a diagnostic test kit for either dry or solution assays. For solution assays, the kit components can be supplied as lyophilized reagents in individual packets having predetermined amounts. Alternatively, they can be provided in bottled or otherwise packaged solutions sufficient in size for one or more assays. Other optional reagents can also be supplied in the kit along with suitable assay utensils or containers for performing the assay. A dry analytical element (described below) containing a ligand analog can also be supplied as part of the diagnostic kit.

Generally, the ligand analog, corresponding receptor and test sample believed to contain a ligand analyte are physically contacted and in a suitable container (e.g. test tube, petrie dish, beaker, cuvette, etc.). The resulting solution can be incubated, if desired, for a time (e.g. 0.5–4 hours) at a temperature of up to about 37° C. to promote the formation of a complex of the receptor with both the ligand analog and the ligand in the test sample. The sample is then evaluated by measuring the fluorescence of bound (i.e. complexed) or unbound (i.e. noncomplexed) label. Such an evaluation can be done visually or with suitable fluorometric detection equipment and procedures.

The method of this invention can also be utilized with a dry analytical element which can be composed of an absorbent carrier material, i.e. thin sheet of self-supporting absorbent or bibulous material, such as a filter paper or strip, which contains the labeled physiologically reactive species of this invention. Such elements can also contain a receptor for a specific binding assay immobilized in a suitable manner and kept isolated from the corresponding ligand analog prior to the assay. Such elements are known in the art as test strips, diagnostic elements, dip sticks, diagnostic agents and the like.

When employed in dry analytical elements, the ligand analog of this invention can be incorporated into a suitable absorbent carrier material by imbibition or impregnation, or can be coated on a suitable absorbent material. Useful carrier materials are insoluble and maintain their structural integrity when exposed to water or physiological fluids such as urine or serum. Useful carrier materials can be prepared from paper, porous particulate structures, cellulose, porous polymeric films, wood, glass fiber, woven and nonwoven fabrics (synthetic and nonsynthetic) and the like. Useful materials and procedures for making such elements are well known in the art as exemplified by U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Patent 2,052,057 (published Jan. 21, 1981).

Preferably, the dry analytical elements of this invention have at least one porous spreading zone as the absorbent carrier material. This zone can be a self-supporting (i.e. composed of a material rigid enough to maintain its integrity), but preferably it is carried on a separate supporting substrate (commonly called a support). Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (reflection or transmission spectroscopy). Useful support materials include paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum or urine is to be assayed.

Useful spreading zones can be prepared using fibrous materials, either mixed with a suitable binder material or woven into a fabric, as described in U.S. Pat. No. 4,292,272 (issued Sept. 29, 1981 to Kitajima et al). Alternatively the spreading zone is prepared from polymeric compositions (e.g. blush polymers) or particulate materials, with or without binding adhesives, as described in U.S. Pat. Nos. 3,992,158 (issued Nov. 16, 1976 to Przybylowicz et al) and 4,258,001 (issued Mar. 24, 1981 to Pierce et al). Other useful spreading zone materials are described in W. German OLS No. 3,150,102 (published July 29, 1982) and Japanese Patent Publication No. 57(1982)-101760 (published June 24, 1982). It is desirable that the spreading zone be isotropically porous, meaning that the porosity is the same in each direction in the zone as created by interconnected spaces or pores between particles, fibers, polymeric strands, etc.

The elements can have one or more reagent zones, spreading zones, registration zones, mordant zones, radiation-blocking or filter zones, subbing zones, barrier zones, buffer zones, etc. The zones are generally in fluid contact with each other meaning that fluids, reagents and reaction products can pass between superposed regions of adjacent zones. Stated in another manner, fluid contact refers to the ability to transport components of a fluid between the zones in fluid contact. Preferably, the zones are separately coated layers, although two or more zones can be a single layer, or a zone can contain two or more separate layers.

The fluorescent labeled ligand analog of this invention can be incorporated in any zone of the element. Alternatively, it can be added to the test sample which is subsequently applied to the element, or the ligand analog can be separately (either subsequently or simultaneously) added to the element with the test sample. The receptor corresponding to the ligand to be determined can also be in any zone of the element in immobilized form, or added to the element simultaneously with the test sample. If both the ligand analog and the receptor are incorporated into the element, they must be kept isolated from each other until the assay is carried out.

In the elements of this invention, the coverage of the ligand analog can be varied widely, but it is generally present in a coverage of up to about 1, and preferably from about $10^{-6}$ to about 1 g/m$^2$. The receptor can be present in a coverage of up to about 200, and preferably from about 40 to about 200 g/m$^2$. A variety of other desirable, but optional, reagents and addenda can be present in the element in amounts known to one skilled in the art. Such materials include interactive reagents, surfactants, buffers, binders, pigments, activators, etc.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, determination of a ligand is made by taking the element from a supply roll, chip packet or other source and physically contacting it with a sample (e.g. 1–100 μl) of the liquid to be tested in the presence of the receptor. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result. Determination of the ligand is achieved by measuring the fluorescence of either the bound (i.e. complexed) or unbound (i.e. noncomplexed) labeled ligand analog.

The following examples are presented to illustrate the practice of the present invention. In these examples, the materials were obtained as follows: Brij ™ 98 surfactant from ICI Americas, Inc. (Wilmington, Del.), Surfactant 10G ™ from Olin Corp. (Stamford, Conn.), bovine gamma globulin from Miles Research Products (Elkhart, Ind.), 1-cyclohexyl-3-(2-morpholinoethyl)carbodiimide metho-p-toluenesulfonate from Bio-Rad Laboratories (Richmond, Calif.), and the remainder were either prepared using conventional techniques or obtained from Eastman Organic Chemicals (Rochester, N.Y.).

EXAMPLE 1

Preparation of Fluorescent Label

Nonionic Surfactant 10G TM (1 g) and water (350 ml) were heated to 95° C. with moderate stirring in a 1 liter flask fitted with an addition flask. In the addition flask, a mixture of styrene (85 g), acrylamide (10 g), methacrylic acid (5 g) $Na_2S_2O_5$ (0.15 g), and $H_2O$ (50 ml) were thoroughly emulsified with 1 g of surfactant 10G TM (50%), and the contents were kept under constant stirring. Polymerization was initiated by adding $K_2S_2O_8$ (0.75 g) and $Na_2S_2O_5$ (0.15 g) into the reaction flask, immediately followed by the addition of the emulsified monomer mixture. Monomer addition was carried out over a 15 to 20 minute period, and polymerization was allowed to continue for an additional 2 hours. The resulting loadable latex was then cooled to room temperature and filtered. After dialyzing against distilled water for about 100 hours, the latex was found to have a total solids content of 8.5%, a pH of 3.6, and a surface tension of 63.2 dynes/cm. Particle sizes were quite uniform (0.09–0.1 μm diameter).

To remove solution polymers and extra surfactant from the latex, the procedure of diafiltration/ultrafiltration was carried out using a conventional diafiltration apparatus having a 300,000 MW cut-off membrane. After about 100 turnovers, the latex was concentrated to about 8% total solids by ultrafiltration. Alternatively, the latex can also be purified by repeating the procedures of centrifugation and redispersing several times using a conventional Beckman preparative ultracentrifuge operated at 40,000 rpm under vacuum (5° C.) for a one-hour period, and the supernatant decanted. The polymer particles can be redispersed with distilled water and the process repeated for three or four more times. The following Table I shows the effects of diafiltration or ultracentrifugation on the analyzed water phase polymers.

TABLE I

| % Solids (Total) | % Aqueous Phase Polymer | % Methacrylic Acid* in Aqueous Phase |
|---|---|---|
| 20.2 (Original) | 2.07 | 0.35 |
| 13.1 (Diafiltered) | 0.034 | 0 |

*Free or polymerized methacrylic acid dissolved in the aqueous phase.

The above results indicated that essentially no free methacrylic acid was left in the aqueous phase after purification.

An acetone solution of europium chelate at 0.5% by weight was prepared by dissolving 0.8695 g of europium-thenoyl trifluoroacetonate ($10^{-3}$ mole) and 0.7732 g of trioctylphosphine oxide ($2 \times 10^{-3}$ mole) in acetone and adjusting the total weight to 328.5 g with an additional amount of acetone.

Fifty grams of the resulting solution was diluted with 20 ml of acetone. Purified latex containing 5 g of polymer was also diluted to 65.6 g with water, and was then added to the $Eu^{+3}$ chelate solution with moderate stirring. Acetone was subsequently removed under vacuum at 60° C. A good dispersion resulted after filtering through a coarse paper. No coagulum was collected. The weight percent of stable fluorescent label of the final dispersion was 8.0%.

EXAMPLE 2

Preparation of Another Fluorescent Label

Following the procedures of Example 1, a stable latex of poly(styrene-co-methacrylamide-co-methacrylic acid (85:10:5 weight ratio) was obtained with 21.6% solids. The latex was diluted to 10% solids and centrifuged at 45,000 rpm to obtain a purified latex essentially free of methacrylic acid to the water phase. A europium chelate was "loaded" into the latex particles using the procedures described in Example 1 to provide a stable fluorescent label.

EXAMPLE 3

Preparation of Labeled Ligand Analog

The preparation of fluorescent labeled thyroxine analog involves a two-step procedure: synthesis of a L-thyroxine-bovine gamma globulin conjugate followed by the attachment of the conjugate to a fluorescent latex label as prepared in Example 1.

The conjugates can be prepared in varying hapten:protein ratios, e.g. 1:1, 2:1, etc., depending on the molar ratio of constituents used. A description of the hapten:protein conjugate having a 1:1 ratio is described below.

The mole ratio of L-thyroxine ($T_4$) to bovine gamma globulin (BGG) was determined either by spectrophotometric analysis on a conventional Cary 219 spectrophotometer or by iodine analysis. Percent iodine determined by reaction activation analysis. Liquid chromatographic analysis for free thyroxine was performed on a conventional Lichrosorb 11 μRP8 4.6×250 mm column using 2% phosphoric acid and acetonitrile as the mobile phase.

A. Direct Coupling of $T_4$-BGG

L-thyroxine was coupled directly to BGG by means of amide bond formation according to the following equation:

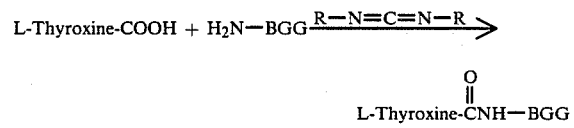

In 300 ml of stirred deionized water, 1.0 g ($6.7 \times 10^{-6}$ mole) of BGG was dissolved. The pH of the solution was adjusted to 7.5 with 0.3 normal sodium hydroxide. In 20 ml of N,N-dimethylformamide, 0.08 g ($1.0 \times 10^{-4}$ mole) of thyroxine was added. The pH of the stirred mixture was raised with a 0.3 normal sodium hydroxide solution until all of the thyroxine had dissolved.

After 0.08 g ($1.9 \times 10^{-4}$ mole) of 1-cyclohexyl-3-(2-morpholinoethyl)carbodiimide metho-p-toluenesulfonate was added to the stirred protein solution, the thyroxine solution was added dropwise. The pH of the reaction mixture was maintained between 7.5 and 8.0 during the addition, and was stirred at pH 7.5 for 24 hours at room temperature and dialyzed against running distilled water for hours. Dialysis was continued against 4 1 of 1% bovine serum albumin (BSA) solution for 24 hours followed by an hour against running distilled water. The freeze-dried conjugate weighed 0.85 g. A mole ratio of thyroxine to BGG of 3 was determined by spectrophotometric analysis.

In a stirred mixture composed of 40 ml of N,N-dimethylformamide and 120 ml of deionized water, a 0.4 g sample of conjugate was dissolved. The solution was dialyzed against 4 l of distilled water at pH 7.5 (containing 4.5 g of 8-anilino-1-naphthalenesulfonic acid) for 48 hours followed by dialysis against running distilled water for 72 hours. The dialyzate was freeze-dried yielding 0.37 g of conjugate. Calculated analysis of iodine for thyroxine:BGG=1 is 0.33. The analysis found was 0.22. The free thyroxine content was determined to be less than 0.1% by liquid chromatographic analysis.

B. Indirect Attachment of Thyroxine to BGG

Alternatively, $T_4$ was also coupled to BGG through a triethylenetetraamine extender attached to a carbohydrate portion of the BGG according to the following equations:

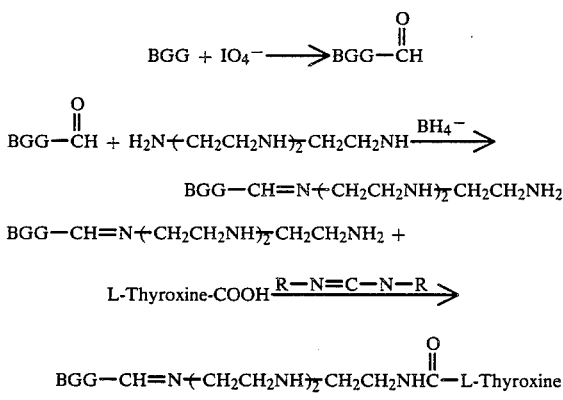

In 20 ml of sodium acetate buffer (0.1 molar, pH 8.0), 0.5 g ($3.6 \times 10^{-6}$ mole) of BGG was dissolved. To the stirred solution was added 40 ml of 0.02 molar sodium periodate solution at pH 8.0. The reaction mixture was stirred for 3 hours at room temperature, then 3 ml of ethylene glycol was added, and stirring was continued for 45 minutes.

Triethylenetetraamine (2 ml) was added to the reaction mixture, and stirring was continued for 72 hours at room temperature. Sodium borohydride (0.4 g) was added, and stirring was continued for 2 hours. The reaction mixture was dialyzed against running distilled water for 48 hours.

The dialyzate was diluted to 150 ml and 0.06 g ($1.4 \times 10^{-4}$ mole) of 1-cyclohexyl-3-(2-morpholinoethyl)carbodiimide metho-p-toluenesulfonate was added. After the carbodiimide had dissolved, the pH of the reaction mixture was adjusted to 7.5 with a 0.3 normal sodium hydroxide solution, and 0.01 g ($1.2 \times 10^{-5}$ mole) of thyroxine dissolved in 20 ml of N,N-dimethylformamide (DMF) was added dropwise (addition of 0.3 normal sodium hydroxide was necessary to dissolve the thyroxine in DMF). During the addition, the pH of the reaction mixture was maintained at 7.5 by addition of dilute hydrochloric acid. An additional 0.05 g of carbodiimide was added, and the reaction mixture was stirred for 18 hours at room temperature. The reaction mixture was dialyzed for 48 hours against 4 liter of distilled water followed by 72 hours against a 1% BSA solution. The freeze-dried product weighed 0.39 g. Calculated analysis of iodine for a mole ratio of thyroxine:BGG of 2 is 0.67. The analysis found was 0.56.

C. Attachment of Conjugates to Fluorescent Label

Directly coupled conjugates having a thyroxine:BGG ratio of 2:1 or 1:1 were attached to the label of Example 1 through amide bond formation between the amino groups of the protein and the carboxylic acid groups on the latex. Carbodiimide was used as the condensing agent.

The molar ratio of conjugate to latex was varied in the reaction mixture between 17.5 and 140 as shown in Table II below. Unreacted carboxylic acid groups on the surface of the latex were blocked by treatment with ethanolamine after reaction of the latex with the conjugate.

In 24 ml of deionized water, adjusted to pH 7.7, 5.3 ml of the label from Example 1 (8% solids, $3.2 \times 10^{-9}$ mole) was added. The pH of the stirred suspension was readjusted to 7.7, and 0.0084 g ($1.9 \times 10^{-5}$ mole) of 1-cyclohexyl-3-(2-morpholinoethyl)carbodiimide metho-p-toluenesulfonate was added, followed by 0.068 g ($4.5 \times 10^{-7}$ mole) of thyroxine-BGG. The reaction mixture was shaken at 11° C. for 48 hours. Ethanolamine (0.1 ml) was added, and shaking was continued for 24 hours. The reaction mixture was placed on a $2.5 \times 24$ cm Bio-Gel A5M chromatographic column and eluted with pH 7 water. The chromatography was repeated. The eluate was filtered twice through Whatman No. 1 filter paper, then concentrated on a conventional ultrafiltration apparatus (0.05 µm membrane). The product was washed with 200 ml of pH 7 water during the concentration (50 ml portion at a time). The final volume of latex was 9 ml having 1.9% solids. Table II below presents results of attachment of the conjugate to the latex particles at various conjugate:latex ratios.

TABLE II

| L-Thyroxine-Bovine Gamma Globulin ($Eu^{+3}$) Latex Label | | | | |
|---|---|---|---|---|
| Thyroxine:BGG (mole:mole) | Thyroxine-BGG:Latex-$Eu^{+3}$ (mole:mole) | Yield of Latex (percent) | Percent Iodine Calc | Percent Iodine Found |
| 2 | 140 | 36 | 0.23 | 0.10 |
| 2 | 70 | 95 | 0.11 | 0.02 |
| 2 | 35 | 97 | 0.06 | 0.04 |
| 2 | 17.5 | 68 | 0.03 | 0.01 |
| 1 | 140 | 65 | 0.23 | 0.02 |
| 1 | 17.5 | 37 | 0.03 | 0.02 |

For optimum interaction of this immunoreagent with thyroxine-antibody, the distribution of thyroxine (antigen) on the protein is such that not all of the amino acid molecules are located on that portion of protein in contact with the surface of the latex label. Purification of the conjugate from free L-thyroxine was performed, since free amino acid (amino acid not covalently bound to protein) could interfere with the immunochemical reaction.

EXAMPLE 4

Dry Test Element for the Fluorometric Determination of Protein

Bovine gamma globulin (BGG) was used as the protein analyte (antigen) to demonstrate the use of the fluorescent labels.

Attachment of BGG to Label

In 48 ml of stirred deionized water adjusted to pH 7.7, bovine gamma globulin (0.136 g, $9 \times 10^{-7}$ mole) was dissolved. To the stirred solution 1-cyclohexyl-3-(2- morpholinoethyl)carbodiimide metho-p-toluenesulfonate (0.0168 g, $3.9 \times 10^{-5}$ mole) was added followed by 10.6 ml of label from Example 1 (8% solids). The pH of the stirred suspension was readjusted to 7.7 and the mixture was shaken at 11° C. for 24 hours.

Solid bovine serum albumin (0.12 g) was added and the reaction mixture was shaken at 11° C. for an additional 24 hours. The reaction mixture was then passed through a 2.5×25 cm Bio-Gel A5M chromatographic column using pH 7 water to elute the latex. The column procedure was repeated with a freshly prepared column. The eluate was filtered twice through Whatman No. 1 filter paper and concentrated to 10 ml on a conventional ultrafiltration apparatus (0.05 μm membrane). During the concentration, 200 ml of pH 7 water was passed through the cell 50 ml at a time. The final 10 ml volume was found to have a 7.2% solids content.

Element Format

| Polystyrene beads coated with Anti-BGG Antibody | 66 g/m² |
|---|---|
| / / / / / / Support / / / / / / | |

One sample of the element shown above was spotted with 5 μl of fluorescent label latex. Another element sample was spotted with 5 μl of 0.2 molar glycine-acetate buffer (pH 7). The remaining element samples were spotted with both $10^{-9}$ molar fluorescent label-BGG analog and BGG (analyte) at a concentration of from $10^{-4}$ to $10^{-9}$ molar. The element samples were incubated for 1-3 minutes after which a wash solution comprising 0.2 molar glycineacetate, 0.1 molar NaCl and 1.0% Brij ™ 98 surfactant at pH 7.0 was applied to each sample for about 30 seconds. Fluorescent measurements of bound label were made using time-delayed luminescence on a modified conventional Ferrand fluorometer. A dose response curve generated from the data showed that the element sample spotted with label alone had the highest amount of fluorescence, and that in the other element, the measured fluorescence decreased with increasing concentration of BGG analyte.

EXAMPLE 5

Stability Comparison

This example illustrates the improved stability of a labeled ligand of this invention by comparing it to similar labeled ligands described and taught in U.S. Pat. No. 4,283,382 (noted above), but which are outside the scope of this invention. This comparison was carried out in the following manner.

Fluorescent labels ($Eu^{+3}$ chelate) were prepared according to the teaching of U.S. Pat. No. 4,283,382 using poly (styrene-co-methacrylic acid) (95:5 weight ratio) (latex 1) and poly(styrene-co-acrylamide) (90:10 weight ratio) (latex 2). The label of this invention prepared in Example 1 was compared to latices 1 and 2. All three labels were stored at 10° C. for several months after which they were evaluated for stability.

Large aggregations of precipitated latex were observed in both labels prepared according to the art (latices 1 and 2), while substantially no aggregations were observed in the label of this invention.

The invention has been described in detail with particular reference to preferred embodiments thereof, but it will be understood that variations and modifications can be effected within the spirit and scope of the invention.

We claim:

1. A fluorescent label comprising a fluorescent rare earth chelate incorporated into a polymeric particle which is derived from a loadable latex having a discontinuous phase and an aqueous phase,
    said discontinuous phase consisting essentially of a polymer comprising:
    (a) from about 50 to about 96 weight percent of recurring units derived from a water-insoluble ethylenically unsaturated polymerizable monomer,
    (b) from about 2 to about 30 weight percent of recurring units derived from a nonionic water-soluble or water-dispersible ethylenically unsaturated polymerizable monomer, and
    (c) from about 2 to about 20 weight percent of recurring units derived from an anionic ethylenically unsaturated polymerizable monomer containing at least one carboxy group.

2. The label of claim 1 wherein the chelate is a chelate of europium or terbium and a 1,3-diketone, phthalate, naphthoate, dipyridine, terpyridine or phenanthroline chelating agent.

3. The label of claim 1 wherein said polymer comprises from about 75 to about 92 weight percent of (a), from about 5 to about 15 weight percent of of (b), and from about 3 to about 10 weight percent of (c).

4. The label of claim 3 wherein said polymer is poly(styrene-co-acrylamide-co-methacrylic acid).

* * * * *